US00PP09328P

United States Patent [19]

Zary

[11] Patent Number: Plant 9,328

[45] Date of Patent: Oct. 17, 1995

[54] HYBRID TEA ROSE PLANT NAMED 'JACCREAM'

[75] Inventor: Keith W. Zary, Thousand Oaks, Calif.

[73] Assignee: Bear Creek Gardens, Inc., Medford, Oreg.

[21] Appl. No.: 366,244

[22] Filed: Dec. 28, 1994

[51] Int. Cl.[6] ..... A01H 5/00

[52] U.S. Cl. ..... Plt./14

[58] Field of Search ..... Plt./11, 14, 15

*Primary Examiner*—Howard J. Locker

*Attorney, Agent, or Firm*—Klarquist Sparkman Campbell Leigh & Whinston

[57] ABSTRACT

A hybrid tea rose plant characterized particularly as to novelty by the unique combination of its excellent production of medium to long stems, its bright white flowers, its strong flower fragrance, its thick petals, its long vase life, and its vigorous, upright growth.

1 Drawing Sheet

The present invention relates to a new and distinct variety of rose plant of the hybrid tea class which was originated by me by crossing the variety ARObipy, U.S. Plant Pat. No. 6,714, with the variety INTERval, U.S. Plant Pat. No. 5,648.

The primary objective of this breeding was to produce a new rose variety having the white flower color of the female parent and its long stems, combined with the thick petals and strong fragrance of the male parent. The objective was substantially achieved, along with other desirable improvements, as evidenced by the following unique combination of characteristics that are outstanding in the new variety and that distinguish it from its parents, as well as from all other varieties of which I am aware:

1. A strong fragrance;
2. Thick petals;
3. Long stems;
4. White flowers;
5. Good vase life;
6. Excellent production when forced in a greenhouse; and
7. Vigorous, upright growth.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—ARObipy, U.S. Plant Pat. No. 6,714.

*Pollen parent.*—INTERval, U.S. Plant Pat. No. 5,648.

Classification:

*Botanical.*—*Rosa hybrida.*

*Commercial.*—Hybrid tea.

FLOWER

Observations made from specimens grown in a greenhouse environment at Somis, Calif. in March through August, 1994.

Blooming habit: Continuous.

Bud:

*Size.*—1½ to 1¾ inches long when the petals start to unfurl.

*Form.*—The bud form is pointed ovoid.

*Color.*—When sepals first divide, bud color is Green-White Group 157B. When half blown, the upper sides of the petals are White Group 155B; and the lower sides of the petals are White Group 155B.

*Sepals.*—Color: Green Group 138B. Surface texture: Covered in fine hairs. There are three normally to occasionally heavily appendaged sepals. There are two unappendaged sepals with hairy edges.

*Receptacle.*—Color: Green Group 137C. Shape: Funnel. Size: Broad; ½ inch by ⅜ inch. Surface: Smooth with a few small glands.

*Peduncle.*—Length: 2¼ to 2¾ inches. Surface: Smooth with a few small glands. Color: Medium green. Strength: Stiff, erect.

Bloom:

*Size.*—Large. Average open size is 5 inches.

*Borne.*—Singly.

*Stems.*—Long to medium. Average length is about 20 to 26 inches.

*Form.*—When first open: High centered. Permanence: Retains its form to the end, and outer petals curl back.

*Petalage.*—Number of petals under normal conditions: 30 to 35.

*Color.*—The upper side of each petal is White Group 155B. The reverse side of each petal is White Group 155B. The base of each petal has a small, ¼ inch by ¼ inch, light greenish yellow (Green-Yellow Group 1D), half-moon at its point of attachment. The major color on the upper side is White Group 155B.

*Variegations.*—Often a greenish yellow streak down the mid-rib of the guard petals.

*Discoloration.*—The general tonality at the end of the first day: No change. At the end of the third day: No change.

*Fragrance.*—Strong.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: 7 days. As a cut flower: 9 to 10 days.

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Greenish white.

Form: Bush.

Growth: Very vigorous; upright; branching. Height and width at the end of one year in the greenhouse equal to 6 to 7 feet by 4 feet. Plant produces 180 to 190 stems per square meter.

Foliage: Number of leaflets on normal mid-stem leaves: 5 or 7.

*Size.*—6 inches by 4½ inches.

*Quantity.*—Normal.

*Color.*—New foliage: Greyed-Red Group 178A. Old foliage: Upper side Green Group 139A. Lower side Green Group 139B.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium; serrated, bearded.

*Disease resistance.*—Resistant to mildew under normal growing conditions at Somis, Calif. greenhouse.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, straight.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its excellent production of medium to long stems, its bright white flowers, its strong flower fragrance, its thick petals, its long vase life, and its vigorous, upright growth.

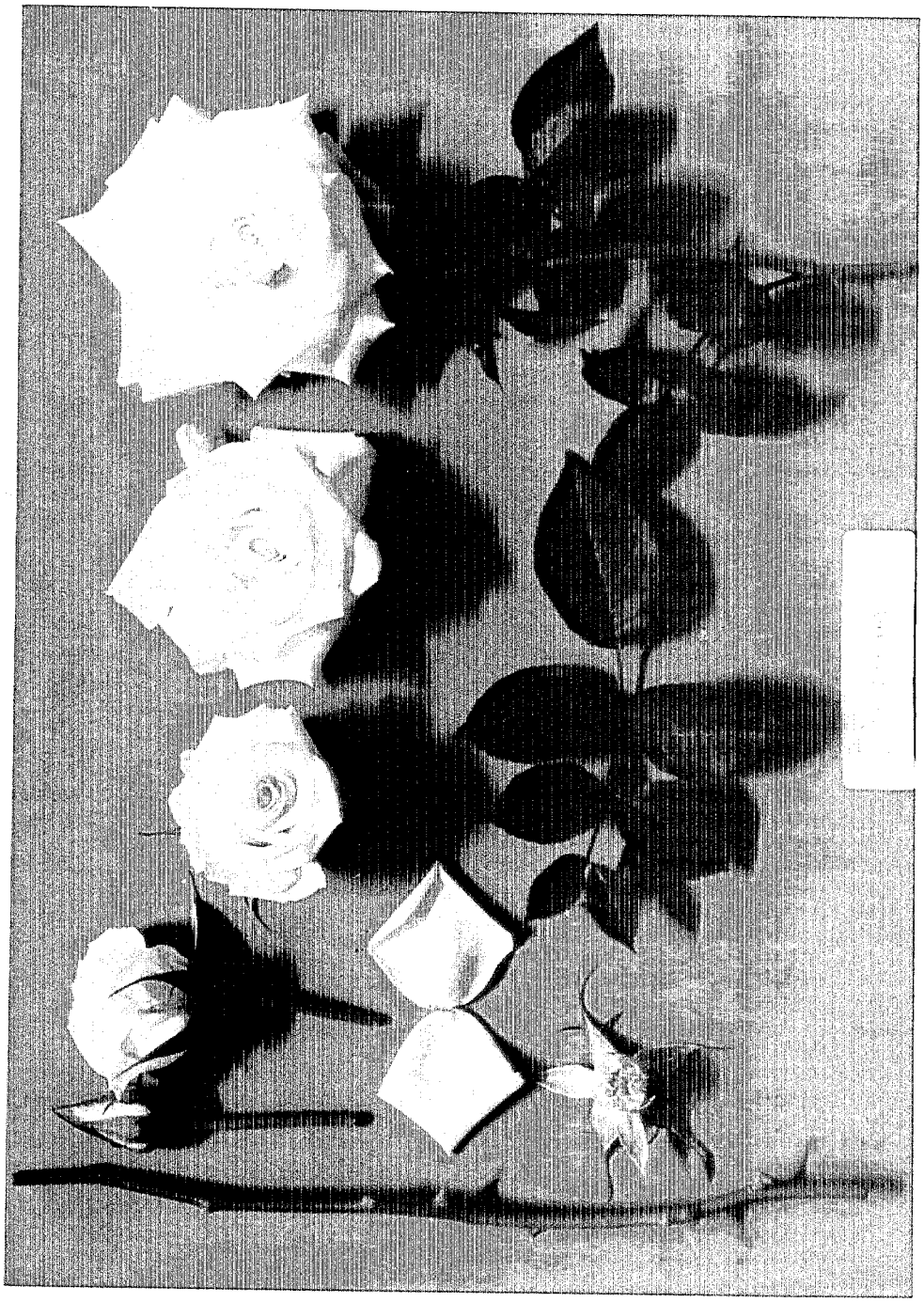

* * * * *